United States Patent [19]
Lunardi-Iskandar et al.

[11] Patent Number: 5,677,275
[45] Date of Patent: Oct. 14, 1997

[54] TREATMENT OF CANCER WITH HUMAN CHORIONIC GONADOTROPIN

[75] Inventors: Yanto Lunardi-Iskandar, Gaithersburg; Robert C. Gallo, Bethesda; Joseph L. Bryant, Rockville, all of Md.

[73] Assignee: The United States of America as represented by the Department of Health and Human Services, Washington, D.C.

[21] Appl. No.: 286,299

[22] Filed: Aug. 5, 1994

[51] Int. Cl.$^6$ ............................ A61K 38/16; C07K 17/00
[52] U.S. Cl. .................... 514/8; 514/12; 514/800; 530/324; 530/397; 530/398
[58] Field of Search .................... 514/8, 12, 800; 530/397, 398, 324

[56] References Cited

U.S. PATENT DOCUMENTS 5,372,996  12/1994  Cabrie ........................................ 514/15

FOREIGN PATENT DOCUMENTS

WO86/04241  7/1986  WIPO.
WO91/16921  11/1991  WIPO.

OTHER PUBLICATIONS

Mann et al, *Scand. J. Clin. Lab. Invest.*, Suppl. vol. 216, pp. 97–104, 1993.
Bidart et al., *TEM*, vol. 4, No. 9, pp. 285–291, 1993.
Siemen, *Rodent Tumor Models in Experimental Cancer Therapy*, Edited by Kallman, Pergamon Press, pp. 12–15, 1987.
Trott, *Rodent Tumor Models in Experimental Cancer Therapy*, Edited by Kallman, Pergramon Press, pp. 6–11, 1987.
Curti, *Critical Reviews in Oncology/Hematology*, vol. 14, pp. 29–39, 1993.
Jain, *Scientific American*, pp. 58–65, Jul. 1994.
Ross et al., *Immunology Today*, vol. 11, No. 6, 1990.
Alfthan et al. (1992) *Cancer Res.* 52: 4628–4633.
Bagshawe (1992) *Acta Oncol.* 31: 99–106.
Bidart, J-M et al., "Human Chorionic Gonadotropin Molecular Forms, Detection, and Clinical Implications." *TEM* 4:285 (1993).
Birken, S. et al., "Structure of the Human Chorionic Gonadotropin β–Subunit Fragment from Pregnancy Urine." *Endocrinology* 123:572 (1988).
Bourinbaiar, A.S. et al., "Inhibitory effect of human chorionic gonadotropin (hCG) on HIV–1 transmission from lymphocytes to trophoblasts." *FEBS LETTERS* 309:82 (1992).
Bourinbaiar, A.S. et al., "Pregnancy hormones, estrogen and progesterone, prevent HIV–1 synthesis in monocytes but not in lymphocytes." *FEBS LETTERS* 302:206 (1992).
Chen, W. et al., "Recombinant Carbohydrate Variant of Human Choriogonadotropin β–Subunit (hCGβ) Descarboxyl Terminus (115–145)." *Journal of Biological Chemistry* 266:6246 (1991).

Cole, Laurence A. et al., "The Heterogeneity of Human Chorionic Gonadotropin (hCG). III. The Occurrence and Biological and Immunological Activities of Nicked hCG." *Endocrinology* 129:1559 (1991).
Cole, L.A., et al., "The Deactivation of hCG by Nicking and Dissociation" *Journal of Clinical Endocrinology and Metabolism* 76:704 (1993).
Danforth, D.N., Jr., M.D., "How Subsequent Pregnancy Affects Outcome in Women with a Prior Breast Cancer." *Oncology* 5:23 (1991).
Elford et al. (1993) *AIDS* 7: 1667–1671.
Freireich, E.J. et al., "Quantitative Comparison of Toxicity of Anticancer Agents in Mouse, Rat, Hamster, Dog, Monkey, and Man." *Cancer Chemotherapy Reports* 50:219 (1966).
Hirabayashi, M., M.D., "Early Gastric Cancer and a Concomitant Pregnancy", *The American Surgeon* 53:730 (1987).
Huang, J. et al., "Amino/Carboxyl–terminal Deletion Mutants of Human Choriogonadotropin β." *The Journal of Biological Chemistry* 268:9311 (1993).
Huang, J. et al., "Mutagenesis of the 'determinant loop' region of human choriogonadotropin β." *Molecular and Cellular Endocrinology* 90:211 (1993).
Kumar, S. et al., "Necrosis and Inhibition of Growth of Human Lung Tumor by Anti–α–Human Chorionic Gonadotropin Antibody." *J. Natl Cancer Inst.* 84:42 (1992).
Loosfelt, H. et al., "Cloning and Sequencing of Porcine LH–hCG Receptor cDNA: Variants Lacking Transmembrane Domain." *Science* 245:525 (1989).
Mann et al. (1993) *Scand. J. Clin. Lab. Invest. Suppl.* 216: 97–104.
Marcillac et al. (1992) *Cancer Res.* 52: 3901–3907.
McFarland, K.C. et al., "Lutropin–Choriogonadotropin Receptor: An Unusual Member of the G Protein–Coupled Receptor Family." *Science* 245:494 (1989).
Nakhai, B. et al., "Over–expression and characterization of recombinant beta subunit of the human chorionic gonadotropin hormone synthesized in insect cells infected with a genetically engineered baculovirus." *Indian Journal of Biochemistry & Biophysics* 29:315 (1992).
Northfeldt et al. (1991) *Hematology/Oncology Clinics of North America* 5: 297–310.
Ozturk, M. et al., "Physiological Studies of Human Chorionic Gonadotropin (hCG), αhCG, and βhCG as Measured by Specific Monoclonal Immunoradiometric Assays." *Endocrinology* 120:549 (1987).

(List continued on next page.)

*Primary Examiner*—Cecilia J. Tsang
*Assistant Examiner*—Abdel A. Mohamed
*Attorney, Agent, or Firm*—Townsend and Townsend and Crew LLP

[57] ABSTRACT

Methods useful for treating cancers are disclosed. The methods involve administering human chorionic gonadotropin (hCG) or human luteinizing hormone (hLH) to patients having cancers. Articles of manufacture that are useful for carrying out the described methods are also described. The claimed methods are effective against breast, prostate, ovary, and stomach carcinomas, as well as neuroblastomas, and Kaposi's sarcoma, among others.

7 Claims, 2 Drawing Sheets

OTHER PUBLICATIONS

Ozturk, M. et al., "Ectopic β-Human Chorionic Gonadotropin Production by a Human Hepatoma Cell Line (FOCUS): Isolation and Immunochemical Characterization." *Endocrinology* 120:559 (1987).

Pierce and Parsons (1981) *Ann. Rev. Biochem.* 50: 465.

Ryan et al. (1988) *FASEB J.* 2: 2661–2669.

Sridhar, P. et al., "Differential secretion and glycosylation of recombinant human chorionic gonadotropin (βhCG) synthesized using different promoters in the baculovirus expression vector system." *Gene* (Netherlands) 131:261 (1993).

Stenman et al. (1993) *Scand. J. Clin. Lab. Invest. Suppl.* 216: 42–78.

Strickland et al. in *Luteinizing hormone action and receptors*, M. Ascoli, Ed., CRC Press, Boca Raton FL, 1985, p. 1.

Ward et al. in *Reproduction in Domestic Animals*, 4th ed., Cuppos, PT, ed., pp. 25–80, Academic Press, NY (1991).

Wass, M. et al., "Response of lymphocytes from cancer patients to human *chorionic* gonadotrophin", Lancet (England) 1:8004:171 (1977).

Yano, T. et al., "Inhibition of human epithelial ovarian cancer cell growth in vitro by agonistic and antagonistic analogues of luteinizing hormone–releasing hormone." *Proc. Natl. Acad. Sci. USA* 91:1701 (1994).

1: KS 4 p9
2: KSY-1 p35
3: KS N1512 PRIMARY CELLS
4: KS N1540 PRIMARY CELLS
5: KS N1542 PRIMARY CELLS
6: KS N1543 PRIMARY CELLS
7: KS N1544 PRIMARY CELLS
8: COLON.CA/NJ

TREATMENT OF CANCER WITH HUMAN CHORIONIC GONADOTROPIN

BACKGROUND OF THE INVENTION

Treatment of tumors, including cancers, is an area of clinical medicine that remains fraught with complications and often presents an array of suboptimal treatment choices. A major problem in treating cancer is that most or all of the known therapies have serious adverse side effects. For example, surgery is commonly employed to remove a cancer from a patient. However, surgery often disfigures the patient or interferes with normal bodily functions. Other treatments such as chemotherapy and radiation treatment also cause undesired side effects.

Kaposi's sarcoma (KS) is one example of a cancer that is difficult to treat. Kaposi's sarcoma is the most common malignancy in patients with acquired immunodeficiency syndrome (AIDS) in the United States. KS occurs in approximately 30% of male AIDS patients, but only 3% of female AIDS patients [Elford et al. (1991) AIDS 7: 1667–1671]. The exact mechanism by which KS develops is unknown. Kaposi's sarcoma is a multifocal neoplasm, consisting of several cell types and abundant angiogenesis. The tumor cell is believed to be a spindle-shaped cell and is usually considered to be of endothelial origin [Rutgers et al. (1986) Am. J. Pathol. 122: 493–499]. However, its precise cellular origin and even its classification as a true monoclonal malignancy versus a polyclonal hyperplasia have remained elusive [Shaw et al. (1984) Science 226: 1165–1171; Holden et al. (1989) J. Invest. Dermatol. 93: 119S–124S; Hashimoto et al. (1987) Pathol. Res. Pract. 182: 658–668].

Existing Kaposi's sarcoma treatments often cause myelotoxicity and neurotoxicity [see, e.g. Northfeldt et al. (1991) Hematology/Oncology Clinics of North America 5: 297–310, which is incorporated herein by reference]. Presently available Kaposi's sarcoma therapies can also induce immunosuppression, compounding the pre-existing immunodeficiency that is usually present in AIDS patients.

Thus, a great need exists for a treatment for Kaposi's sarcoma and other cancers that does not cause severe adverse side effects. Hormonal treatments offer promise of such a treatment.

Many cancers secrete hormones such as human chorionic gonadotropin (hCG) and/or an hCG subunit. Indeed, elevated hCG serum concentration is considered a reliable indicator of the presence of some tumors [see, e.g., Bagshawe (1992) Acta Oncol. 31: 99–106; Stenman et al. (1993) Scand. J. Clin. Lab. Invest. Suppl. 216: 42–78; Mann et al. (1993) Scand. J. Clin. Lab. Invest. Suppl. 216: 97–104]. Elevated serum levels of hCG or an hCG subunit are found in patients having gestational trophoblastic tumors and testicular germ cell tumors, as well as nongonadal and nontrophoblastic tumors such as cancers of the bladder, pancreas, cervix, lung, liver, and stomach [Bidart et al. (1993) TEM 4: 285–291; Marcillac et al. (1992) Cancer Res. 52: 3901–3907; Alfthan et al. (1992) Cancer Res. 52: 4628–4633].

Human chorionic gonadotropin belongs to a family of glycoprotein hormones, human luteinizing hormone (lutropin, hLH), follitropin (FSH), and thyrotropin (TSH). Each of these hormones is composed of two dissimilar, noncovalently bound subunits, α and β. The hormones share a common α subunit, while the β subunits differ slightly in length and amino acid sequence [Ryan et al. (1988) FASEB J. 2: 2661–2669; Ward et al. in Reproduction in Domestic Animals, 4th ed., Cuppos, PT, ed., pp. 25–80. Academic Press, NY (1991)]. The most closely related of the β subunits are those of hCG and hLH, which are 85% identical, except for an approximately 20 amino acid extension on the carboxy terminus of hCG. Indeed, hCG and hLH act through a common receptor [Loosfelt et al. (1989) Science 245: 525–528; McFarland et al. (1989) Science 245: 494–499] and elicit identical biological responses [Pierce and Parsons (1981) Ann. Rev. Biochem. 50: 466; Strickland et al. in Luteinizing hormone action and receptors, M. Ascoli, Ed., CRC Press, Boca Raton Fla., 1985, p. 1]

The present invention is based on the discovery that hCG and related hormones are useful not only as a marker for detecting cancers, but also as a treatment for cancers. Provided herein are an effective methods for treating cancers using human hormones such as human chorionic gonadotropin or human lutropin, and articles of manufacture that are useful for carrying out these methods.

SUMMARY OF THE INVENTION

The invention provides methods for treating a cancer in a patient. The methods involve administering to the patient a therapeutically effective amount of a pharmaceutical agent selected from the group consisting of human chorionic gonadotropin, human lutropin (hLH), a β subunit of hCG or hLH, and a biologically active fragment of hCG, hLH, or a β-subunit of hCG or hLH. Also provided are articles of manufacture that include packaging material and a pharmaceutical agent contained within the packaging material, wherein the pharmaceutical agent is therapeutically effective for treating a cancer and is selected from the group consisting of human chorionic gonadotropin (hCG), human lutropin (hLH), a β-subunit of hCG or hLH, and a biologically active fragment of hCG, hLH, or a β-subunit of hCG or hLH. The packaging material includes a label which indicates that the pharmaceutical agent is useful for treating a malignant neoplastic disease.

DESCRIPTION OF THE SPECIFIC EMBODIMENTS

Definitions

Figure 1A:
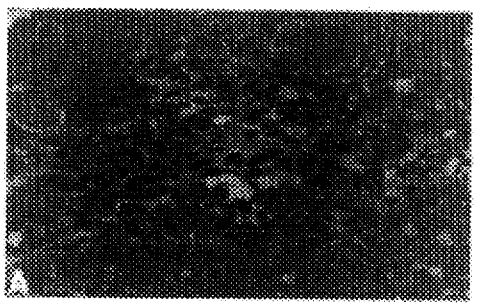
FIG. 1 show that tumor cells undergo apoptosis when treated with hCG. The experimental protocol is as described in Example 6. A) FIG. 1A Tumor from a mouse that had not been treated with hCG has many mitotic figures when stained with the hematoxylin and eosin stains. [See, e.g., Biological Staining Methods, George D. Jurr Div., Baird & Tatlock, Romford UK (1969)]. B) FIG. 1B Thin tissue section of a tumor from a mouse that had been treated with hCG (100 USP units injected subcutaneously daily for 7 days) shows areas that have few cells, and other areas exhibit dense nuclear masses. 1C, 1D Tumors from hCG-treated mice were stained in situ to detect the presence of DNA fragmentation. Apoptotic cells are brown, while normal viable cells appear blue after staining.
Figure 1B:
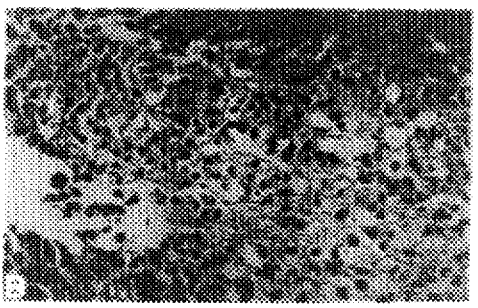
Figure 1C:
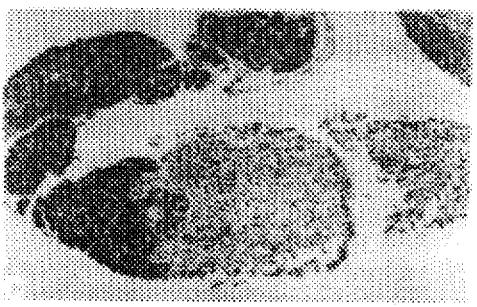
Figure 1D:
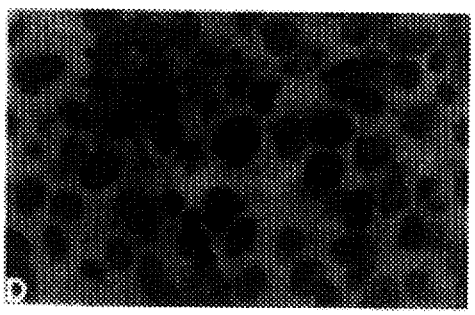

A cell line is said to be "malignant" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes. A tumor is said to be "long-lasting" when the tumor persists in an animal for at least about one month.

The term "effective amount" means a dosage sufficient to produce a desired result. The desired result can be subjective or objective improvement in the recipient of the dosage, a decrease in tumor size, a decrease in the rate of growth of cancer cells, or a decrease in metastasis.

The terms "treating cancer", "therapy", and the like mean generally a treatment that causes any improvement in a mammal having a cancer wherein the improvement can be ascribed to treatment with the hormone polypeptide. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical exam, laboratory parameters, tumor markers, or radiographic findings.

Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonongrams, nuclear magnetic resonance testing and positron emissions testing.

"Inhibiting the growth of cancer cells" can be evaluated by any accepted method of measuring whether growth of the cancer cells has been slowed or diminished. This includes direct observation and indirect evaluation such as subjective symptoms or objective signs as discussed above.

A "hormone-responsive cancer" refers to a cancer that responds to treatment with hCG, hLH, a β-subunit of hCG or hLH, or a biologically active subfragment. To determine whether a cancer is hormone-responsive, the clinician can test whether hormone treatment inhibits growth of cells derived from a cancer of that particular type. Appropriate assays are described below.

A "biologically active fragment" of hCG, hLH, or a β-subunit of hCG or hLH exhibits a biological activity of the indicated hormone. To determine whether a polypeptide fragment is biologically active, one can perform an assay to detect a biological effect that is typical of cells exposed to hCG or hLH, such as stimulation of progesterone or cAMP production. Alternatively, one can test the fragment to determine whether it binds to the lutropin-choriogonadotropin receptor (LH-CG-R). Suitable tests are described below.

Hormone Polypeptides Useful for Treating Cancer

Hormone polypeptides that are useful in the claimed articles of manufacture and methods for treating cancer include both hCG and hLH. Furthermore, the β-subunits of hCG and hLH are useful whether or not complexed to the α-subunit that hCG and hLH share. Also, biologically active fragments of β-hCG and β-hLH also function to treat cancer according to the present invention.

hCG and hLH are available from several sources. For example, hCG and hLH are available commercially from Sigma Chemical Co. (St. Louis, Mo.). hCG is available in a form suitable for therapeutic use from Wyeth-Ayerst Laboratories (APL™, Philadelphia Pa.), Organon, Inc. (Pregnyl™, West Orange, N.J.), and Serono Laboratories, Inc. (Profasi™, Randolph Mass.).

Alternatively, one can isolate the natural hCG and hLH polypeptides from human cells by conventional techniques, such as affinity chromatography. Conveniently, polyclonal or monoclonal immunoglobulins obtained against hCG or hLH can be used to prepare a suitable affinity column by well known techniques [see, e.g., Hudson and May, *Practical Immunology*, Blackwell Scientific Publications, Oxford, United Kingdom, 1980, which is incorporated herein by reference].

One can also produce the hormone polypeptides that are useful in the present invention by chemical or enzymatic synthesis. Techniques for solid phase chemical synthesis of polypeptides are described, for example, in Merrifield, *J. Amer. Chem. Soc.* 85: 2149–2156 (1963), which is incorporated herein by reference. Such chemical synthesis is generally employed for the production of polypeptides of fewer than about 100 amino acids, more usually fewer than about 80 amino acids, and typically fewer than about 50 amino acids.

A preferred method for producing the hormone polypeptides of the invention involves recombinant expression. For this purpose, natural or synthetic nucleic acids that code for the hCG or hLH, or the β-subunit of either hormone, or an active fragment of either hormone, will typically be operably linked to a promoter to form an expression cassette. The α- and β-hCG cDNAs have been cloned and the nucleotide sequences determined [Xia, H., *J. Molecular Endocrinology*, pp. 337–343 (Jun. 10, 1993); Sherman, G. B., *J. Molecular Endocrinology*, pp. 951–959 (Jun. 6, 1992); Segal, S. J. (ed.), Plenum Press, N.Y., pp. 37–51 ( 1980); *Basic and Clinical Endocrinology*, Gieseman, L. K., (ed.), Ch. 20, pp. 543–567 (1991); Ward et al., supra.]. Therefore, one of skill can readily identify and clone the cDNAs that code for these polypeptides. Alternatively, one can synthesize the desired coding regions chemically.

To produce the hormone polypeptides, one introduces an expression cassette that codes for the hormone polypeptide into an appropriate host cell. Suitable host cells include yeast, filamentous fungi, insects (especially employing baculoviral vectors), and mammalian cells, as well as bacterial systems.

Mammalian or insect cell expression systems are preferred, since protein folding, transport and processing (including glycosylation) closely approximate that which occurs in the human [see, e.g., E. Winnacker, *From Genes to Clones*, VCH Publishers, New York (1987), which is incorporated herein by reference]. For examples of suitable expression systems for the hormone polypeptides useful in the present invention, see, e.g., Corless et al. (1987) *J. Biol. Chem.* 262: 14187–14203; Lustbader et al. (1987) *J. Biol. Chem.* 262: 14204–14212; Huang et al. (1993) *Mol. Cell. Endocrinol.* 90: 211–218; Reddy et al. (1985) *Proc. Natl. Acad. Sci. USA* 8: 3644–3648; all of which are incorporated herein by reference.

The baculovirus expression system is most preferred, producing the hormone polypeptides in relatively high yields, and in an active form. See, e.g., Nakhai et al. (1992) *Indian J. Biochem & Biophys.* 29: 315–321.

Once expressed, one can purify the hormone polypeptides from lysed cells or, preferably, from culture medium into which the hormone polypeptides are secreted. Standard procedures of the art are suitable, including ammonium sulfate precipitation, affinity columns, column chromatography, gel electrophoresis and the like (see, generally, R. Scopes, *Protein Purification*, Springer-Verlag, N.Y. (1982), which is incorporated herein by reference). Substantially pure hormones of at least about 90 to 95% homogeneity are preferred, and those of 98 to 99% or greater homogeneity most preferred, for pharmaceutical uses.

Once purified, partially or to homogeneity as desired, the hormones can then be used therapeutically.

It is recognized that amino acid residues in the hormone polypeptides may be replaced by other amino acid residues with similar chemical properties (e.g., charge or hydrophobicity). Because the substituted amino acids have similar properties, the substitutions do not change the functional properties of the polypeptides. The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

Identifying Biologically Active Hormone Fragments

Hormone polypeptides that are effective against cancers include the intact hCG and hLH dimers, the β-subunits of hCG and hLH, and subfragments of the hCG and hLH β-subunits. The hCG and hLH α-subunits alone are not effective. Among the biologically active subfragments of β-hCG that are effective against cancer are β-hCG(109–145) [Stevens (1986) *CIBA Foundation Symp*. 19: 200–225] and β-hCG(109–119) [Lyer et al. (1992) *Int. J. Peptide Prot. Res*. 39: 137–192]. These latter polypeptides are available commercially from Bachem Bioscience, Inc. (King of Prussia, Pa.), and β-hCG(109–145) is also available from Sigma Chemical Co.

So long as the polypeptide or subfragment retains biological activity, it can be used in the claimed cancer treatment methods. To determine whether a particular polypeptide is biologically active, cells that express the hLH-hCG receptor (LH-CG-R) are exposed to the polypeptide fragment being tested, after which the cells are assayed for biological effects that are indicative of hCG or hLH presence. One can conduct this assay using a mammalian cell line that naturally expresses the LH-CG-R. One such cell type that is useful for this assay is the MA-10 transformed murine Leydig cell line [Ascoli (1981) *Endocrinology* 108: 88–95]. The MA-10 cells are grown as described by Chen and Puett [(1991a) *J. Biol. Chem*. 266: 6904–6908; Chen and Puett (1991b) *Biochemistry* 30: 10171–10175; Chen et al. (1991) *J. Biol. Chem*. 266: 19357–19361].

As an alternative to cells that naturally express LH-CG-R, one can use cells that express LH-CG-R because the cells have been transfected with an expression vector that harbors the LH-CG-R gene or cDNA. A suitable expression vector and cell line, as well as the nucleotide sequence of the LH-CG-R cDNA, are described in McFarland et al. (1989) *Science* 245: 494–499.

LH-CG-R-expressing cells exposed to a biologically active fragment of hCG or hLH will have elevated concentrations of cyclic AMP (cAMP). cAMP assays are described in, for example, McFarland et al., supra., Ascoli et al. (1989) *J. Biol. Chem*. 264: 6674, and Segaloff and Ascoli (1981) *J. Biol. Chem*. 256: 11420. A biologically active hormone fragment will cause cells treated with 10 ng/ml of the fragment for 15 minutes at 37° C. to have cAMP levels at least about 1.5 times as great as cells not treated with the fragment.

Another commonly used assay is to determine whether cells treated with the polypeptide produce higher levels of progesterone than untreated cells. The hormone polypeptide is added at various concentrations to the cells in a suitable medium. After a four hour incubation at 37°, progesterone is measured by radioimmunoassay. Basal progesterone concentration for untreated MA-10 cells is typically less than 10 ng/ml, while cells incubated in the presence of a biologically active hormone polypeptide will typically produce at least 500 ng/ml progesterone [Huang et al. (1993) *J. Biol. Chem*. 268: 9311–9315].

An alternative assay to assess whether a hCG or hLH polypeptide or subfragment is biologically active is to determine whether the polypeptide binds to the cellular receptor for hCG and hLH. A suitable assay is described in Huang et al., supra.

Testing for Efficacy Against a Particular Cancer

The claimed methods and articles of manufacture are effective against a range of different cancer types. For example, many neoplasms are amenable to treatment using the claimed invention. These neoplasms include gestational trophoblastic tumors and testicular germ cell tumors, as well as nongonadal and nontrophoblastic tumors such as cancers of the breast, bladder, pancreas, cervix, lung, liver, ovary, colon, and stomach. Patients having these types of cancers typically exhibit elevated serum levels of hCG and/or/ β-hCG. See, e.g., Bidart, supra; Marcillac et al., supra.; and Alfthan et al., supra.

The invention is also useful for treating neuroblastomas and Kaposi's sarcoma. Cancers that are particularly susceptible to the claimed treatment methods are Kaposi's sarcoma, neuroblastoma, and carcinomas of the breast, prostate, ovary, and stomach.

The clinician can test the efficacy of hCG against a particular tumor type, either in vitro or in vivo. For in vitro tests, cells derived from the tumor are grown in the presence or absence of the hormone and the effect of the hormone is determined. One commonly utilized assay for tumor cell growth is the methylcellulose assay [Lunardi-Iskandar et al. (1985) *Clin. Exp. Immunol*. 60: 285–293]. The cells are plated in medium containing methylcellulose, which prevents nontumor cells from undergoing mitosis and forming colonies. The hormone polypeptides of the invention will prevent tumor cells from forming as many colonies as untreated cells. Another means for measuring the inhibitory effect of the hCG of hLH polypeptides is by measuring the rate of incorporation of radiolabelled metabolites such as tritiated thymidine.

The growth of a cell line is said to be "inhibited" by a hormone treatment if, when assayed by means such as radioisotope incorporation into the cells, the treated cells proliferate at a rate that is less than about 80% of the proliferation rate of untreated control cells, and preferably less than about 70% of the untreated cell proliferation rate. More preferably, the growth rate is inhibited by at least 50%. If growth is assayed by a means such as plating in methylcellulose, the growth of a cell line is said to be "inhibited" if the treated cells give rise to less than about 80% of the number of colonies that grow from a like number of untreated cells. Preferably, the number of colonies from treated cells is less than about 70% of the number from untreated cells. More preferably, the number of colonies is decreased by at least 50%.

In addition to, or instead of, testing a hormone for efficacy against a particular tumor cell type in vitro, the clinician can test the hormone in vivo. For in vivo tests, cells derived from the tumor type are injected into laboratory animals such as immunodeficient mice. Typically, either the laboratory animals or the cells have been pre-treated with the hormone. The animals are then monitored to determine whether tumors arise at the site of injection, or elsewhere in the animal.

One method for carrying out these in vivo tests is as follows. The tumor cells to be tested are grown for 48 hours in RPMI1640+10% fetal calf serum in the presence of 100 USP units/ml hCG per ml. As a control, tumor cells are grown in the absence of hCG. Approximately $5 \times 10^6$ cells are then subcutaneously injected into SCID or nude mice (Beige, BALB/c, Swiss, or NCr [see, e.g., Croyba et al. (1993) *Laboratory Animal Science*, 43: 120–122)]. Alternatively, the efficacy of a hormone against a tumor cell type can be tested by inoculating a mouse with hCG before challenge with the tumor cells, rather than pretreating the cells. For example, mice can be injected with 10–100 USP units hCG daily for 5–7 days before challenge with the tumor cells. One can test mice of either sex, and at various ages (neonate, young, adult).

Laboratory animals that are either treated with a hormone polypeptide prior to tumor cell inoculation, or inoculated with tumor cells that have been grown in the presence of the hormone polypeptide, typically will not develop tumors. For example, in the absence of hCG pretreatment, Kaposi's sarcoma cells will typically induce a strong angiogenic reaction at the site of inoculation within seven days. Tumors will usually develop and persist for at least three months. These tumors can occur at the site of injection and also as metastases in one or more of the lung, spleen, skin, or pancreas. Typically, tumors induced by the KS cell lines will metastasize.

Mice that are injected with Kaposi's sarcoma cells that have been pretreated with hCG, or mice that have been pre-inoculated with hCG before challenge with the Kaposi's sarcoma cells, do not develop tumors within two months post-challenge.

Cancer Therapy Methods and Articles of Manufacture

Pharmaceutical compositions containing the hormone polypeptides described herein are administered to an individual having cancer. In therapeutic applications, compositions are administered to a human patient in an amount sufficient to cause regression of the tumor, or at least partially arrest the tumorigenesis and metastasis. An amount adequate to accomplish this is defined as a "therapeutically effective dose." Amounts effective for this use will depend on, e.g., the nature of the hormone (specific activity, etc.), the manner of administration, the stage and severity of the cancer, the weight and general state of health of the patient, and the judgment of the prescribing physician. Typically, doses will range from about 3000 to about 5000 USP units per patient, (70 kg) per day of hormone polypeptide per day. If a cancer has metastasized a larger dose can be employed. Generally, the dose will be repeated daily until the tumors are gone. Typically, a minimum of one to two weeks of treatment is required.

Single or multiple administrations of the hormone polypeptide compositions can be carried out with dose levels and pattern being selected by the treating physician. In any event, the pharmaceutical formulations should provide a quantity of hormone sufficient to effectively treat the patient. Administration should begin at the first indication of undesirable cellular proliferation or shortly after diagnosis, and continue until symptoms are substantially abated and for a period thereafter. In well established cases of cancer, loading doses followed by maintenance doses will be required.

The clinician can monitor whether a dosage regime is correct by monitoring the concentration of β-hCG in the patient's blood plasma. The experimental data presented herein allows one to ascertain the proper level of β-hCG. As shown in Example 2, serum from human females who are at an early stage in pregnancy inhibits tumor cell growth more effectively than serum from late-pregnancy females. During the early weeks of pregnancy, β-hCG levels increase rapidly, reaching a peak of 160 USP units per ml plasma during the tenth gestational week. β-hCG levels then decline gradually to about 10 USP units per ml in the third trimester of pregnancy. Therefore, regardless of the route of administration, the clinician should adjust the dosage regime as required to maintain plasma β-hCG concentration at a level of at least 10 USP units per ml, and preferably within a range of 100 USP units per ml to 200 USP units per ml. One can assess these levels using the assays described above, or by other methods such as a competitive radioimmunoassay.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. The most preferred route of administration is intralesional or intramuscular injection. The invention provides compositions for parenteral administration which comprise a solution of the hormone dissolved or suspended in an acceptable carrier, preferably an aqueous carrier. A variety of aqueous carriers can be used, e.g., water, buffered water, 0.4% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A preferred composition of hCG is available commercially from several manufacturers (Wyeth-Ayerst Laboratories (APL™, Philadelphia Pa.), Organon, Inc. (Pregnyl™, West Orange, N.J.), and Serono Laboratories, Inc. (Profasi™, Randolph Mass.). These compositions are of sufficient purity for therapeutic use. To prepare the hormone for therapeutic use, the clinician follows the directions provided by the manufacturer. Typically, this involves reconstituting the dried hormone polypeptide in sterile water to obtain the desired concentration.

A typical pharmaceutical composition for intravenous infusion could be made up to contain 250 ml of sterile Ringer's solution, and 3000–5000 USP units of hormone polypeptide. Actual methods for preparing parenterally administrable compounds will be known or apparent to those skilled in the art and are described in more detail in for example, *Remington's Pharmaceutical Science*, 17th ed., Mack Publishing Company, Easton, Pa. (1985), which is incorporated herein by reference.

For solid compositions of the hormones of the invention, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more anti-cancer hormones, more preferably at a concentration of 25%–75%.

The present invention also includes an article of manufacture that comprises at least one pharmaceutical agent contained within packaging material. The pharmaceutical agent is therapeutically effective for treating a malignant neoplastic disease and is selected from the group of hormone polypeptides disclosed herein. This group consists of human chorionic gonadotropin (hCG), human lutropin (hLH), a β-subunit of hCG or hLH, or an active fragment of one of these hormone polypeptides.

The packaging material comprises a label which indicates that the pharmaceutical agent can be used for treating a malignant neoplastic disease. The packaging material will usually also include instructions for administering the pharmaceutical agent, as well as a list of cancers against which the pharmaceutical agent is effective.

The following examples are provided by way of illustration and are not intended to limit the scope of the claims.

EXAMPLE 1

Pregnant Mice are Resistant to Tumorigenesis Induced by Kaposi's Sarcoma Cell Line To demonstrate that pregnant mice are resistant to tumorigenesis, we injected Kaposi's sarcoma cells into mice at various stages of pregnancy. $5 \times 10^7$ Kaposi's sarcoma cells (KS-Y-1) were injected into BG-nude or Scid immunodeficient mice. nude mice (Beige, BALB/c, Swiss, or NCr (see, e.g., Croyba et al. (1993) *Laboratory Animal Science*, 43: 120–122). Mice were either early in pregnancy ($\leq 10$ days gestation), late in pregnancy ($\geq 16$ days gestation), or not pregnant. One month after inoculation, mice were sacrificed and examined for the presence of tumors.

Results are shown in Table 1. None of the mice injected with Kaposi's sarcoma cells while early in pregnancy developed tumors. In contrast, both of the non-pregnant mice developed metastatic tumors. Mice that had been injected late in pregnancy developed tumors, although these tumors were much smaller than those in non-pregnant mice, and did not metastasize.

TABLE 1

Inhibition of tumor growth induced by KS Y-1 cell in immunodeficient mice during pregnancy.

| Animal (#) | Inoculation (Gestation day #) | Tumor size (mm) | Angiogenesis | Metastasis |
|---|---|---|---|---|
| early stage | | | | |
| Bg (4) | 6–10 | 0 | – | – |
| Scid (3) | 5–10 | 0 | – | – |
| late stage | | | | |
| Bg (3) | 16–18 | 1 × 1 to 2 × 2 | + | – |
| Scid (3) | 16–18 | 1 × 1 to 3 × 2 | + | – |
| Bg | Non Pregnant | 25 × 20 | + | + |
| Scid | Non Pregnant | 27 × 22 | + | + |

$5 \times 10^6$ KS Y-1 cells were injected intraperitoneally into early (3 to 10 days) and late stage (14 to 17 days) pregnant immunodeficient mice (Beige-xid-nude: Bg-nude; Scid: severe combined immunodeficient mice). The mice were sacrificed 1 month post-inoculation. Metastasis was defined by the presence of characteristic tumors in lung, pancreas and colon.

EXAMPLE 2

Serum from Pregnant Females Inhibits Growth of Kaposi's Sarcoma Cells in vitro

This example demonstrates that serum from pregnant mouse and human females inhibits the growth of tumor cells. We assayed the ability of Kaposi's sarcoma (KS Y-1) cells to grow in the presence of serum obtained from pregnant females. We tested both human and murine serum, obtained either early or late in pregnancy.

$5 \times 10^6$ cells/ml KS Y-1 were seeded in methylcellulose in the presence or absence of serum from pregnant females. We utilized the method described in Lunardi-Iskandar et al. (1985) *Clin. Exp. Immunol.* 60: 285–293. Results are shown in Table 2. The number of colonies formed is inversely proportional to the inhibitory effect of the pregnancy serum. These results demonstrate that serum obtained from human or murine females early in pregnancy is highly effective in inhibiting growth of Kaposi's sarcoma cells in vivo. Late pregnancy serum is slightly less effective than early pregnancy serum, but nevertheless exhibits an inhibitory effect compared to serum from males and non-pregnant females.

TABLE 2

Sera of pregnant mice and humans inhibits in vitro colony formation of KS Y-1 cells.

| Cells | Source of serum | Serum-free 0% | Early pregnancy* | | | Late pregnancy* | | |
|---|---|---|---|---|---|---|---|---|
| | | | 1% | 5% | 10% | 1% | 5% | 10% |
| KS Y-1 | | 191 | | | | | | |
| | mouse A | | 40 | 4 | 0 | 146 | 108 | 70 |
| | B | | 36 | 2 | 0 | 138 | 102 | 69 |
| | C | | 41 | 7 | 0 | 140 | 105 | 67 |
| | D | | 31 | 10 | 0 | ND | ND | ND |
| | Human A | | 23 | 11 | 3 | 169 | 142 | 92 |
| | B | | 21 | 12 | 5 | 165 | 102 | 74 |
| | C | | 34 | 7 | 0 | 167 | 121 | 75 |
| | D | | 32 | 13 | 3 | 157 | 120 | 73 |
| ATL1 | | 310 | | | | | | |
| | mouse A | | 293 | 276 | 298 | 283 | 301 | 322 |
| | Human A | | 280 | 269 | 301 | 260 | 273 | 265 |

| | | Sera from non-pregnant individuals | | |
|---|---|---|---|---|
| | | 1% | 5% | 10% |
| KS Y-1 | Male | 193 | 178 | 179 |
| | Non-pregnant female | 177 | 170 | 175 |

KS Y-1 cells were seeded in a methylcellulose (0.8%, v/v) clonogenic assay in the presence of an increasing percentage (v/v) of serum from pregnant women or mice. Colonies (>50 cells) were counted following a 10 day incubation period. Number of colonies are expressed as mean number of colonies per $5 \times 10^4$ cells seeded in triplicate cultures. The standard deviation did not exceed 10% of the mean values. ATL 1 is an human adult T-cell leukemia line.

EXAMPLE 3

Inhibition of Tumor Cell Growth In Vitro by hCG

In this Example, we demonstrate that hCG inhibits growth of Kaposi's sarcoma cells in vitro. We tested the ability of the Kaposi's sarcoma cell line KS Y-1 to form colonies in methylcellulose in the presence of hCG. Four different forms of hCG were tested: intact native hCG (includes both α- and β-subunits), native β-hCG, β-hCG$_{(109-145)}$ (a fragment consisting of amino acids 109–145 of β-hCG), and α-hCG.

We plated KS Y-1 or control cells ($5 \times 10^5$ cells/ml) in methylcellulose, using the protocol of Lunardi-Iskandar et al. (1985) *Clin. Exp. Immunol.* 60: 285–293. Cells were incubated at 37° for 48 hr, after which colonies were counted. Results are shown in Table 3, expressed as number of colonies per $5 \times 10^4$ cells plated. Concentrations of hCG are in µg/ml.

Native hCG, the β-subunit of hCG alone, and βhCG$_{(109-145)}$ all inhibited growth of KS Y-1 cells in a dose-dependent manner. βhCG and βhCG$_{(109-145)}$ completely inhibited colony formation at 10 µg/ml. αhCG caused, at most, a slight decrease in number of colonies formed. None of the hCG preparations inhibited colony formation by the control adult T-cell leukemia cell line (ATL 1) or peripheral blood lymphocytes (PBL).

TABLE 3

Both hCG or βhCG block KS Y-1 cell growth in a methylcellulose clonogenic assay.

| Cells | Treatment (μg/ml hCG) | | | | | | | |
|---|---|---|---|---|---|---|---|---|
| | None | hCG | βhCG native | | βhCG$_{109-145}$ | | αhCG | |
| | | 12.5 | 1 | 10 | 1 | 10 | 1 | 10 |
| KS Y-1 | 234 | 10 | 24 | 0 | 34 | 0 | 224 | 179 |
| ATL 1 | 310 | 267 | 289 | 267 | 299 | 278 | 298 | 285 |
| PBL | 320 | 319 | 287 | 290 | 301 | 315 | 818 | 330 |

KS Y-1 cells were seeded in methylcellulose in the presence of hCG, native βhCG, βhCG synthetic peptide$_{109-145}$ or αhCG. The hCG preparation contains both α- and β-hCG. ATL1 is a human adult T-cell leukemia line. Numbers indicate number of colonies per 50,000 cells plated.

hCG also inhibits the uptake of $^3$H-thymidine into Kaposi's sarcoma cells. This provides further demonstration of the inhibitory effect of hCG on KS cell proliferation. The cells were cultured in flat bottomed 96-well tissue culture plates (3072, Falcon Labware) at various cell densities in RPMI1640+FCS medium in the presence or absence of hCG. Proliferation was evaluated by a 4 hr pulse of $^3$H-thymidine (Amersham, Arlington Heights Ill.) added at 48 hr after culture initiation. Thymidine incorporation was reduced by about 80% in cells grown in the presence of 10 and 100 USP units hCG per ml.

EXAMPLE 4 hCG Inhibits Tumorigenesis and Metastasis in vivo

To demonstrate that hCG inhibits tumorigenesis and metastasis in vivo, we injected KS Y-1 cells that had been treated with KS Y-1 into immunodeficient mice. We grew KS Y-1 cells in RPMI 1640 medium containing 10% fetal calf serum, 1% penicillin/streptomycin, and 1% glutamine for 48 hr in the presence of 10 USP units hCG per ml. The treated cells (5×10$^5$) were then injected into Bg-Nude mice.

For two months post-injection, mice were analyzed for the presence of tumors. Results are presented in Table 4. Each of the control mice (injected with cells that had not been pretreated with hCG) had tumors, while no tumors were observed in the mice that received hCG-treated KS Y-1 cells. We observed metastasis in the control mice, as tumors arose at sites other than the site of injection.

TABLE 4

In vitro pretreatment of KS Y-1 cells With hCG inhibits angiogenesis and metastasis in Bg-nude mice.

| Cell treatment | Tumor size (mm) | Angiogenesis | Metastasis |
|---|---|---|---|
| No treatment (n = 7) | 17 × 22 to 27 × 30 | + | + |
| hCG source A (n = 6) | 0* | − | − |
| hCG source B (n = 6) | 0* | − | − |

5 × 10$^6$ KS Y-1 cells were treated for 48 h with control (PBS) or 10 USP units/ml hCG from source A (Sigma: CG-10) or source B (Ayerst Lab: APL ™) before subcutaneous injection into Bg-nude mice. Animals were sacrificed at 6 weeks post inoculation.
n = number of animals in test group.
*No tumors were observed by macroscopic or light microscopic evaluation of the injection site within 6 weeks post-injection.

EXAMPLE 5 hCG Pretreatment of Mice Inhibits Tumorigenesis

To further demonstrate that hCG inhibits tumorigenesis in vivo, we injected mice with hCG prior to challenge with Kaposi's sarcoma cells. Mice were injected with hCG (100 USP units) daily for seven days. After this pretreatment, 10$^5$ KS Y-1 cells in 0.1 ml were injected subcutaneously or intraperitoneally into each mouse. The mice were examined for presence of tumors, angiogenesis and metastasis at 3–4 weeks post inoculation.

The results of these experiments are shown in Table 5. Half of the mice that had been pretreated with hCG did not develop tumors, while the tumors that arose in the remaining pretreated mice were much smaller than the tumors found in mice that had not been pretreated.

TABLE 5

In vivo pretreatment of immunodeficient mice (Balb/c nude) with hCG inhibits tumorigenesis induced by KS Y-1 cells.

| Treatment, administration | Tumor size (mm) | Angiogenesis | Metastasis |
|---|---|---|---|
| Human hCG source A, subcutaneous (n = 6) | 0 × 0 | | |
| | 0 × 0 | | |
| | 0 × 0 | | |
| | 2 × 3 | + | − |
| | 1 × 2 | + | − |
| | 2 × 2 | + | − |
| Human hCG source B, intraperitoneal (n = 6) | 0 × 0 | | |
| | 0 × 0 | | |
| | 0 × 0 | | |
| | 1 × 1 | + | − |
| | 1 × 1 | + | − |
| | 2 × 1 | + | − |
| No treatment, subcutaneous (n = 4) | 45 × 35 | + | + |
| | 41 × 19 | + | + |
| | 42 × 39 | + | + |
| | 39 × 37 | + | + |

Animals were pretreated with hCG 100 USP units (IP or SC) daily for 1 week and then injected with KS Y-1, 10$^5$ cells in 0.1 ml. Source A (Sigma: CG-10), source B (Ayerst Lab: APL ™). The "No treatment" controls consisted of injections of PBS.

EXAMPLE 6 hCG Induces Tumor Regression in vivo

In this Example, we demonstrate that hCG treatment causes regression of established tumors. We intralesionaly or intraperitoneally injected 100 USP units hCG daily for 7 days into mice that had established, metastatic tumors. Tumors had been induced by inoculating immunodeficient mice with KS Y-1 Kaposi's sarcoma cells. Within two weeks after the one week treatment regime ended, the tumors had shrunken significantly, and appeared necrotic. Untreated mice had large, metastatic tumors, and we observed no necrosis of the tumor cells.

To determine the mechanism by which hCG inhibits tumor growth, we compared tumor tissues from mice that had been treated with hCG or β-hCG to mice that had not been treated. Tumor tissues were collected at least one month after inoculation with the Kaposi's sarcoma cell line. Microscopic examination of βhCG-treated tumors showed focal areas containing few cells, the absence of edema, and necrosis. These observations suggested that the tumor cells had been eliminated by an apoptotic process.

To confirm that tumor regression occurred by an apoptotic mechanism, we stained slides of tissues from hCG-treated tumors to detect the presence of DNA fragmentation (DNA laddering) that is characteristic of apoptosis [Cohen (1991) *Adv. Immunol.* 50: 55–85 (1991); Clarke et al. (1990) *Anat. Embryol.* 181: 195–213)]. For this analysis, we employed the ApopTag™ (Oncor, Inc., Gaithersburg, Pa.) in situ apoptosis detection kit according to the instructions supplied by the manufacturer (which are incorporated herein by reference). More than 90% of the cells in regions of the tumors that were regressing were positive for DNA laddering (FIG. 1).

Ninety percent of the tumors from animals treated with hCG expressed genes that are indicative of apoptosis [c-myc, Cohen (1991) *Adv. Immunol.* 50: 55–85; c-rel, Abbabie et al. (1993) *Cell* 75: 899–912]. We also detected the polypeptide gene product of this gene. Tumor cells from animals that had not been treated with hCG did not express this apoptosis gene. Therefore, hCG appears to induce apoptosis in tumor cells.

EXAMPLE 7 hCG Receptor Present Kaposi's Sarcoma Cells

We utilized radiolabelled hCG in chemical crosslinking experiments to detect the presence of the hCG receptor in various cell types. We tested cell lysates of primary cells from the pleural effusion of five Kaposi's sarcoma patients (Patients #1–4), a colon carcinoma patient (#1539), cell line KS Y1 p 35 and strain KS 4 p9 (See FIG. 2). As a positive control we used colon carcinoma hepatoma cell lines and as a negative control we used peripheral blood lymphocytes from normal adults.

The binding of $^{125}$I-hCG to the hCG receptor was performed as described by Sahraoui et al. (1992) *Cellular Immunol.* 139: 318–332. The hCG and receptor were cross-linked by incubating a pellet of $5 \times 10^6$ cells in 50 µl of dimethylsulfoxide in which we had diluted 1 µl of 1 mg/ml disuccinimidyl suberate solution (DSS) in dimethyl sulfoxide. After incubating for 10 min. at 4° C., the reaction is stopped by quenching the unreacted DSS with 10 µl of a 1 mM ammonium acetate solution for one minute. The cells are then washed twice at 4° C. in 10 mM Tris-HCl, pH 7.4, 0.15M NaCl containing 1 µM EDTA. The crosslinked $^{125}$I-hCG-receptor was released from the cells by extracting for 30 min at 4° C. in 0.5% NP40 in 0.05M Tris-HCl, pH 7.4, 0.15M NaCl containing 50 µg/ml aprotinin, 50 µg/ml leupeptin, 0.1% sodium azide, and 10 mM sodium pyrophosphate. The lysates were clarified by centrifugation (15 kRPM for 15 min. at 4° C.) and size-fractionated on a 6% SDS-polyacrylamide gel.

Figure 2:
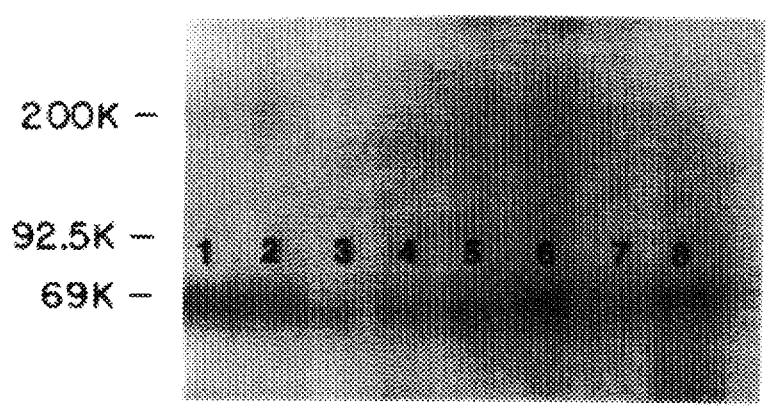
FIG. 2 shows the results of chemical crosslinking experiments in which radiolabelled β-hCG was cross-linked to the hCG receptor, after which cells were lysed and proteins extracted. Lane 1: Kaposi's sarcoma cell strain KS-4 (passage 9); Lane 2: Kaposi's sarcoma cell line KS Y-1 (passage 35); Lanes 3–7: Kaposi's sarcoma cell lines from HIV positive patients; Lane 8: primary colon carcinoma cells from patient #1539.

We detected a 70 kD band that coincides with the M, of β-hCG coupled to its receptor [Hipkin et al. (1993) *Mol. Endocrinol.* 29: 121–125] (FIG. 2). We also tested KS lesions from eight AIDS patients by immunostaining, and detected the presence of the hCG receptor in all eight lesions. These results strongly suggest that the antitumor effect of β-hCG may be a direct consequence of hCG interaction with its receptor, leading to apoptotic cell death.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An article of manufacture comprising packaging material and a pharmaceutical agent contained within the packaging material, wherein the pharmaceutical agent is therapeutically effective for treating Kaposi's sarcoma and is selected from the group consisting of i. human chorionic gonadotropin (hCG);

ii. a β-subunit of hCG and iii. a biologically active fragment of hCG or a β-subunit of hCG;

and wherein the packaging material comprises a label which indicates that about 3000 to about 5000 United States Pharmacopeia ("USP") units per 70 kg body weight per day of the pharmaceutical agent is useful for treating Kaposi's sarcoma.

2. A method for treating Kaposi's sarcoma in a patient, the method comprising administering to the patient about 3000 to about 5000 United States Pharmacopeia ("USP") units per 70 kg body weight per day of a pharmaceutical agent selected from the group consisting of i. human chorionic gonadotropin (hCG);

ii. a β subunit of hCG; and iii. a biologically active fragment of hCG or a β-subunit of hCG.

3. An article of manufacture as in claim 1 wherein the label states that the agent should be administered to a patient to maintain its in vivo concentration at between 100 and 200 United States Pharmacopeia ("USP") units per ml of plasma.

4. An article of manufacture as in claim 3 wherein the label states that the plasma lever of the agent should be administered to a patient to maintain its in vivo concentration at about 160 USP units per ml.

5. A method of claim 2 wherein the agent is administered in an amount sufficient to maintain the concentration of the agent in the patient's plasma between 100 and 200 United States Pharmacopeia ("USP") units per ml of plasma.

6. A method of claim 2 wherein the agent is β-hCG (109–145).

7. A method of claim 2 wherein the agent is β-hCG (109–119).

* * * * *